too_long

INFRARED LASER CATHETER SYSTEM

CROSS REFERENCE TO RELATED APPLICATIONS

This application is a continuation-in-part of my application Ser. No. 014,990 filed Feb. 17, 1987, which is a continuation of my application Ser. No. 761,188 filed July 31, 1985, both now abandoned.

FIELD OF THE INVENTION

This invention relates to laser catheters and optical fiber systems for generating and transmitting energy to a surgical site in a living body for the purposes of tissue removal or repair.

BACKGROUND OF THE INVENTION

While lasers have been used for many years for industrial purposes such as drilling and cutting materials, it is only recently that surgeons have begin to use lasers for surgical operations on living tissue. To this end, laser energy has been used to repair retinal tissue and to cauterize blood vessels in the stomach and colon.

In many surgical situations, it is desirable to transmit laser energy down an optical fiber to the surgical location. If this can be done, the optical fiber can be included in a catheter which can be inserted into the body through a small opening, thus reducing the surgical trauma associated with the operation. In addition, the catheter can often be maneuvered to surgical sites which are so restricted that conventional scalpel surgery is difficult, if not impossible. For example, laser energy can be used to remove atherosclerotic plaque from the walls of the vasculature and to repair defects in small-diameter artery walls.

A problem has been encountered with laser surgery in that prior art lasers which have been used for industrial purposes often have characteristics which are not well suited to percutaneous laser surgery. For example, a laser which is conventionally used for scientific purposes is an excimer laser which is a gas laser that operates with a gas mixture such as Argon-Fluorine, Krypton-Fluorine or Xenon-Fluorine. Another common industrial laser is the carbon dioxide or $CO_2$ laser.

Both the excimer laser and the $CO_2$ laser have been used for surgical purposes with varying results. One problem with excimer lasers is that they produce output energy having a wavelength in the range 0.2-0.5 micrometers. Blood hemoglobin and proteins have a relatively high absorption of energy in this wavelength range and, thus, the output beam of an excimer laser has a very short absorption length in these materials (the absorption length is the distance in the materials over which the laser beam can travel before most of the energy is absorbed). Consequently, the surgical site in which these lasers are to be used must be cleared of blood prior to the operation, otherwise most of the laser energy will be absorbed by intervening blood before it reaches the surgical area. While the removal of blood is possible if surgery is performed on an open area it is often difficult if surgery is to be performed via a catheter located in an artery or vein.

An additional problem with excimer lasers is that the output energy pulse developed by the laser is very short, typically about ten nanoseconds. In order to develop reasonable average power, pulses with extremely high peak power must be used. When an attempt is made to channel such a high peak power output into an optical fiber, the high peak power destroys the fiber. Thus, excimer lasers have a practical power limit which is relatively low. Consequently, when these lasers are used for biological tissue removal, the operation is slow and time consuming.

The $CO_2$ generates output energy with a wavelength on the order of 10 micrometers. At this wavelength, the absorption of blood hemoglobin is negligible but the absorption by water and tissue is relatively high. Scattering at this wavelength is also very low. Although these characteristics of the $CO_2$ laser are favorable for surgical applications, the $CO_2$ laser suffers from the same drawback as excimer lasers in that the absorption length is relatively short due to the high absorption of the laser energy in water. Thus, the surgical area must be cleared of blood prior to the operation.

Unfortunately, the $CO_2$ laser also suffers from a serious additional problem. Due to the long wavelength, the output energy from the carbon dioxide laser cannot be presently transmitted down any optical fibers which are suitable for use in percutaneous surgery (present fibers which can transmit energy from a $CO_2$ laser are either composed of toxic materials, are soluble in water or are not readily bendable, or possess a combination of the previous problems) and, thus, the laser is only suitable for operations in which the laser energy can be either applied directly to the surgical area or applied by means of an optical system comprised of prisms or mirrors.

Accordingly, it is an object of the present invention to provide a laser catheter system which uses laser energy of a wavelength that is strongly absorbed in water, in bodily tissues and atherosclerotic plaque.

It is another object of the present invention to provide a laser catheter system which is capable of providing laser energy that can be transmitted through existing silica-based optical fibers.

It is a further object of the present invention to provide a laser catheter system in which optical scattering is minimized and which has a medium-length absorption length to confine the energy to the area of interest.

It is yet another object of the present invention to provide an optical catheter system with a laser that can be operated on either a pulsed mode or a continuous wave mode.

It is still another object of the present invention to provide a laser catheter system which can be used for biological material removal and biological material repair.

It is still another further object of the present invention to provide a laser catheter system which can be used for removal of atherosclerotic plaque within a living body.

SUMMARY OF THE INVENTION

The foregoing objects are achieved and the foregoing problems are solved in one illustrative embodiment of the invention in which a laser catheter system employs a laser source operating in the wavelength region of 1.4-2.2 micrometers. Illustrative laser sources operating this region are Holmium-doped YAG, Holmium-doped YLF, Holmium doped YSGG, Erbium-doped YAG, Erbium doped YLF and Thulium-doped YAG lasers.

In the inventive laser system, the above-noted lasers are used with a specially-treated silica fiber that has been purified to reduce the concentration of hydroxyl (OH—) ions.

For biological tissue removal, the laser source may be operated in a pulsed mode with a relatively long pulse of approximately 0.2–5 milliseconds at an energy level of approximately 1–2 joules per pulse, for a spot size of the order of 1.5 millimeters in diameter. With this time duration and energy level, the peak power of the laser pulse is approximately 1 kilowatt. This amount of power can easily be tolerated by the silica fiber, but is sufficient for rapid material removal. With a repetition rate in the range of 1–10 hertz, the average power delivered to a surgical site by such a laser will be under 10 watts.

In particular, for removal of atherosclerotic plaque from a living body, particularly satisfactory results are obtained using a Holmium-doped laser source operating in a pulsed mode in a wavelength range of from about 1.90 to about 2.10 micrometers, and at a threshold energy density of at least about 0.6 joules/mm$^2$. The pulse width used should be substantially less than a thermal time constant for plaque, or substantially less than about 83 milliseconds. The repetition rate typically is about 2 Hertz.

Alternatively, for biological tissue repair, the laser source can be operated in a low power continuous wave mode to repair, by coagulation, of tissue by a process similar to "spot welding".

BRIEF DESCRIPTION OF THE DRAWINGS

The objects, advantages, and features of this invention will be more clearly appreciated from the following detailed description when taken in conjunction with the accompanying drawings in which.

DETAILED DESCRIPTION OF THE PREFERRED EMBODIMENT

Figure 1:
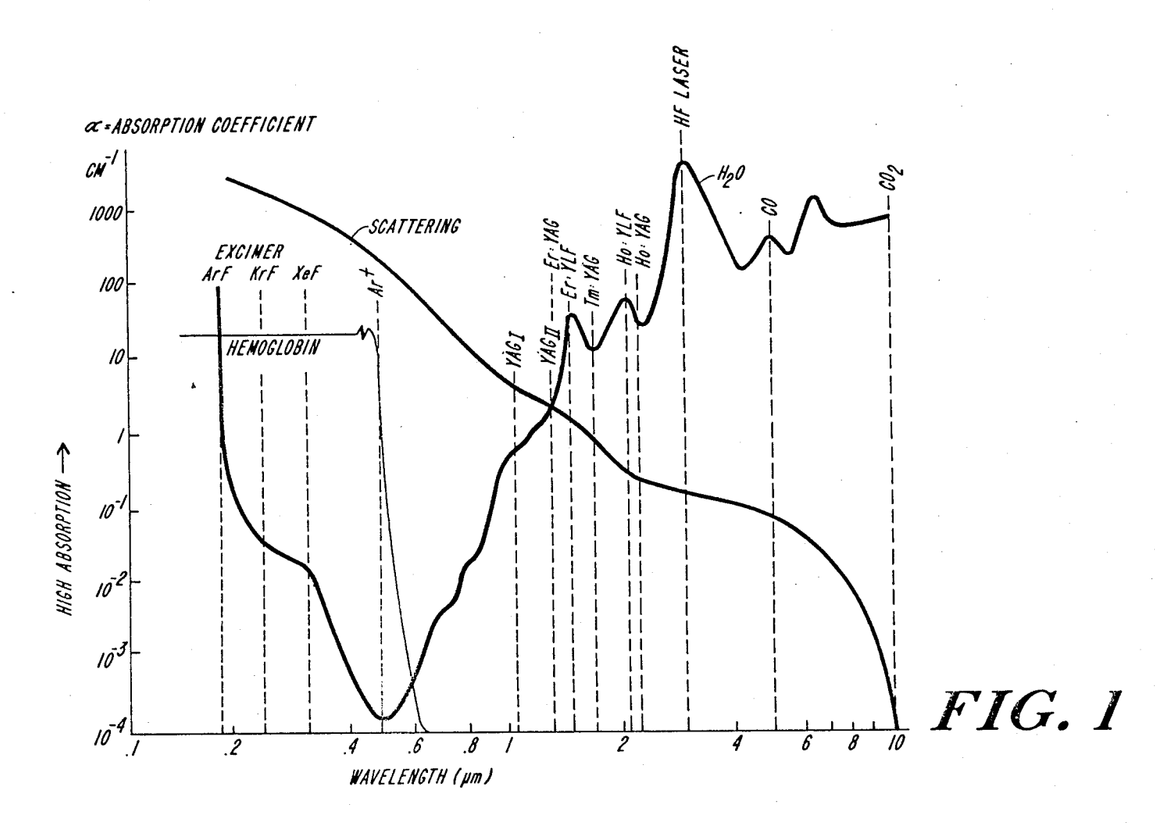
FIG. 1 shows a sketch of absorption of electromagnetic energy versus wavelength and electromagnetic energy scattering versus wavelength.

The absorption and scattering characteristics versus output wavelength of a plurality of known laser systems are shown in FIG. 1. FIG. 1 has a logarithmic scale representing the absorption coefficient in units of cm$^{-1}$ along the vertical axis and the incident energy wavelength in micrometers along the horizontal axis.

From FIG. 1, it can be seen that excimer laser systems which utilize conventional gas mixtures, such as Argon-Fluorine, Krypton-Fluorine and Xenon Fluorine, and Argon gas lasers produce output energy which falls in the 0.2–0.5 micrometer wavelength region. In this region, the absorption of blood hemoglobin and proteins is very high. Consequently, the absorption length is very short (about 5–10 microns) and virtually no blood can be present between the fiber end and the surgical site during the operation. Thus, it is necessary to remove blood from the surgical area when these lasers are used for surgical purposes.

In addition, for lasers such as Argon, the absorption of water reaches a minimum at 0.5 micrometers so that it is necessary to use a higher power laser than is desirable to achieve sufficient power in the surgical area for material cutting and removal. Also, due to the low absorption of the laser output in water and hemoglobin, the absorption length is very long (approximately 1 mm). In addition, scattering for these lasers is relatively high, causing difficulty in controlling the laser energy and a danger of tissue damage outside the surgical area due to scattering of the laser energy.

At the other end of the wavelength spectrum shown in FIG. 1 are carbon monoxide and carbon dioxide lasers producing outputs at 5 and 10 micrometers, respectively. At these wavelengths scattering is negligible and absorption by water and tissue is relatively high and thus both lasers have good surgical properties. Unfortunately, due to the high absorption of water, the absorption length is relatively short (about 20 microns). Further, silica-based optical fibers in present use which are suitable for percutaneous surgical use have a practical "cutoff" in transmission which occurs approximately at 2.3 micrometers, and, thus, the output energy from carbon monoxide and carbon dioxide lasers cannot be transmitted through such an optical fiber.

In accordance with the invention, laser sources of interest are those that lie in the wavelength range of approximately 1.4–2.15 micrometers. As shown in FIG. 1, in this range, the energy absorption of water is relatively high whereas optical scattering is relatively low. Illustrative lasers which are useful with the present invention comprise Erbium-doped Yttrium Aluminum Garnet (YAG) with a wavelength of 1.55 micrometers, Erbium-doped Yttrium Lithium Fluoride (YLF) with a wavelength of 1.73 micrometers, Thulium-doped YAG with a wavelength of 1.88 micrometers, Holmium-doped YLF with a wavelength of 2.06 micrometers, Holmium-doped YAG at a wavelength of 2.1 micrometers, and Holmium-doped Yttrium-Scandium-Gadolinium-Garnet (YSGG) at a wavelength of 2.088 micrometers. The absorption of the laser energy produced by lasers in this latter group by water is moderately high and, consequently, the absorption by biological tissues of such energy will also be relatively high. However, the absorption by water is not as high as the absorption of CO and $CO_2$ laser energy. Thus, the absorption length will be longer for the lasers operating in the 1.4–2.2 micrometer range than for $CO_2$ lasers. Typically, the absorption length in the body for lasers operating in the 1.4–2.2 micrometer range is about 200 microns. Therefore, it is still possible to operate satisfactorily even with 10–30 microns of blood between the fiber end and the surgical site.

Figure 2:
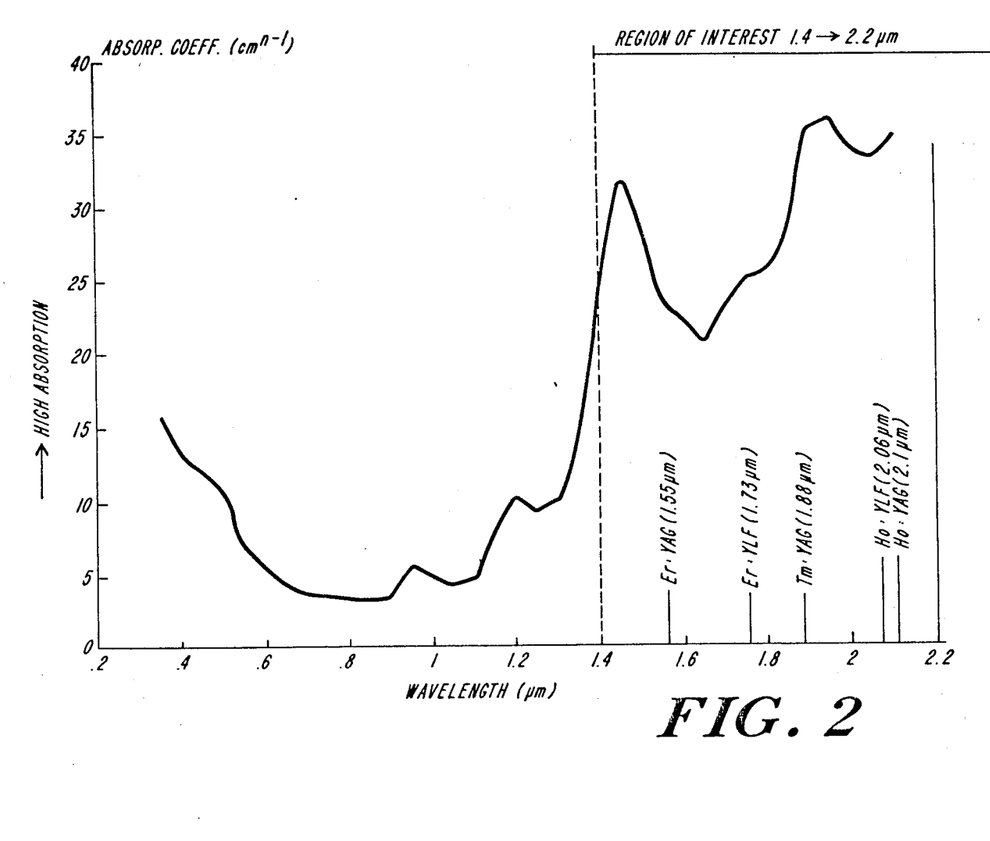
FIG. 2 shows an absorption versus wavelength plot for atherosclerotic plaque obtained in a carotid endarterectomy with the region of interest for the inventive laser sources (1.4–2.2 micrometers) outlined.

Of particular interest is the absorption of the laser energy by atherosclerotic plaque, since an important use of laser catheter systems is angioplasty, particularly the clearing of blocked arteries. FIG. 2 is a plot of the absorption by plaque of electromagnetic energy versus wavelength for energy in the wavelength range of 0.2–2.2 micrometers. As shown in FIG. 2, the absorption by plaque of electromagnetic energy reaches a minimum in the 0.8–1 micrometer wavelength range and generally increases with increasing wavelength in the wavelength region of 1–2.2 micrometers. In the wavelength range from 1.4–2.2 micrometers, the wavelength range produced by laser in the above-mentioned group, the absorption by plaque is at a relatively high value.

Figures 3, 4:
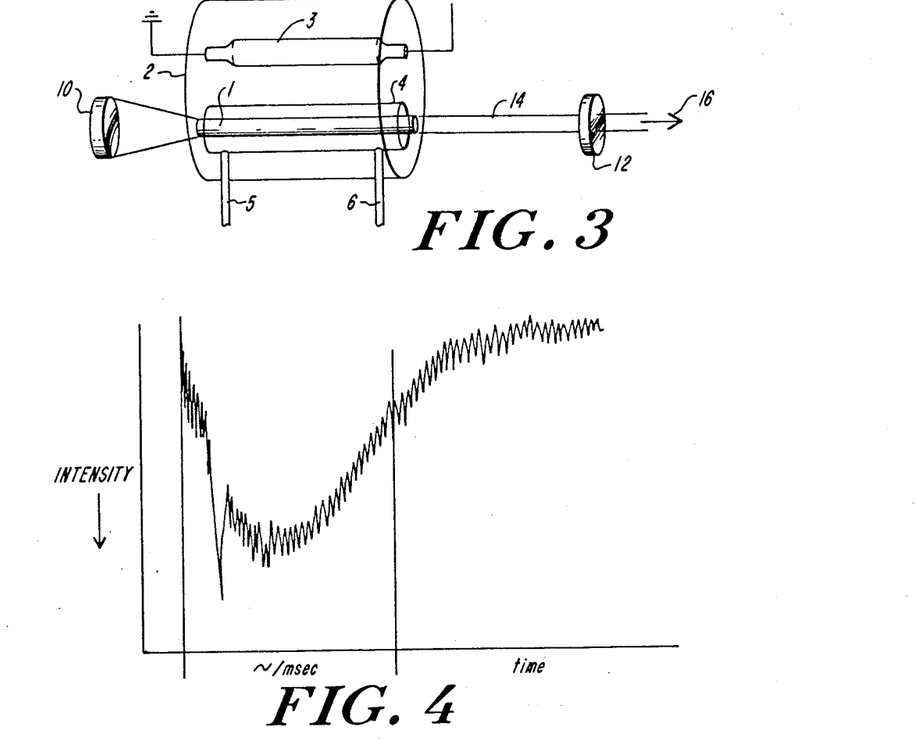
FIG. 3 of the drawing is a schematic diagram of a typical solid state laser construction used in the inventive laser sources.
FIG. 4 of the drawing is a plot of laser output intensity versus time for a typical pulse shape developed by a laser shown in FIG. 3 when used for tissue removal.

A schematic diagram of a typical solid-state laser construction is shown in FIG. 3. The laser assembly consists of a laser crystal 1 and an excitation device such as a flashlamp 3. Typically, for the crystal compositions disclosed above, the laser crystal must be cooled to cryogenic temperatures to provide low laser-threshhold operation. Cryogenic cooling is typically provided by enclosing crystal 1 in a quartz or fused-silica jacket 4 through which liquid nitrogen is circulated. Liquid nitrogen enters jacket 4 by means of an inlet pipe 5 and leaves by means of an outlet pipe 6. The laser cavity is formed by a high reflectivity concave mirror 10 and a partial reflector 12.

Generally, the crystal is excited by optical pumping which is, in turn, accomplished by irradiating the crystal with light from a flashlamp 3. A flashlamp which is typically used with the inventive laser compositions is a high-pressure Xenon flashlamp. Lamp 3 may also be surrounded by a quartz flow tube (not shown) through which coolant is pumped.

Crystal 1 and flashlamp 3 are enclosed in a reflector 2 which concentrates the flashlamp energy into the laser crystal. To maximize energy transfer from lamp 3 to crystal 1, the inner surface of reflector 2 is coated with a material chosen to have high-reflectivity at the pumping wavelength of the laser crystal—illustratively, aluminum or silver. In order to provide thermal insulation to prevent condensation on the system optics, it may be necessary to evacuate the interior of reflector 2 or to provide a vacuum jacket around crystal 1.

The construction of cryogenic solid-state lasers is conventional and described in a variety of sources; accordingly such construction will not be discussed further in detail herein. A more complete discussion of construction details of a typical cryogenic laser is set forth in an article entitled "$TEM_{oo}$ Mode Ho:YLF laser", N. P. Barnes. D. J. Gettemy, N.J. Levinos and J. E. Griggs, *Society of Photo-Optical Instrumentation Engineers*, Volume 190—LASL Conference on Optics 1979, pp 297–304.

FIG. 4 of the drawing is a plot of the illustrative pulse shape developed by a laser in the preferred group when used in the "material removal" mode. FIG. 4 shows light intensity along the vertical axis increasing in the downward direction versus time increasing towards the right. Although, as shown in FIG. 4, the laser source has been adjusted to produce an output pulse of relatively long time duration, most of the output energy is released within approximately 1 millisecond of the beginning of the pulse. It should also be noted, as illustrated in FIG. 4, that lasers in the preferred laser group exhibit a "spiking" phenomenon caused by internal relaxation oscillations in the laser crystal. The spiking behavior causes local increases in laser intensity which have a large magnitude, but a very short time duration. Similar "spiking" behavior has been found advantageous when lasers are used to drill metals and other materials for industrial purposes and it is believed that such "spiking" behavior enhances the laser usefulness for biological material removal.

Figure 5:
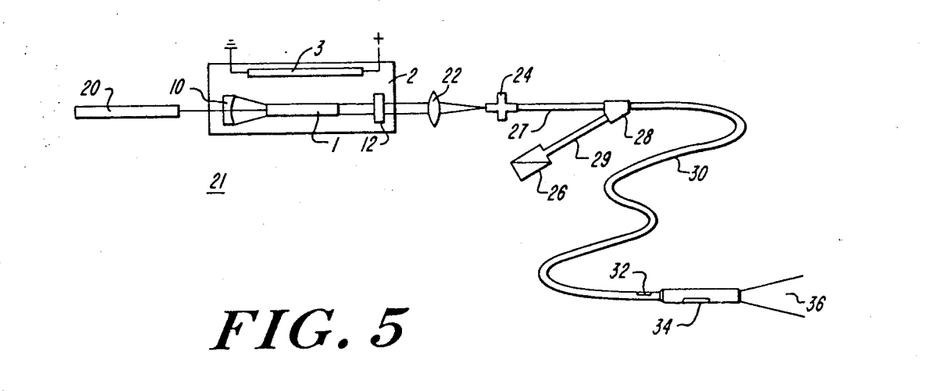
FIG. 5 is a schematic diagram of a laser catheter which employs a single optical fiber for transmitting laser energy to a surgical location.

FIG. 5 is a schematic diagram of a laser/catheter system employing a solid state laser of the type shown in detail in FIG. 3. More specifically, the infrared output energy of laser 21 is focused by a conventional focusing lens onto the end of the optical fiber which is held in a conventional fiber optic connector 24. Fiber optic connector 24 is, in turn, connected to a tube 27 which houses a single optical fiber. Tube 27 is connected to a conventional two-lumen catheter 30 by means of a bifurcation fitting 28.

Illustratively, catheter 30 has two lumens passing axially therethrough to its distal end 34 so that an optical fiber can pass through one lumen and transmit laser energy from fiber optic connector 24 to lens tip 34. As previously mentioned, the optical fiber which passes through the catheter is specially purified to reduce the hydroxyl ion concentration to a low level, thus preventing the laser energy which is transmitted down the fiber from being highly absorbed in the fiber material. A fiber which is suitable for use with the illustrative embodiment is a fused-silica optical fiber part no. 822W manufactured by the Spectran Corporation located in Sturbridge, Mass.

Advantageously, the mirrors and lenses (10, 12 and 22) which are used to form the IR laser cavity and focus the output energy beam are generally only reflective to energy with a wavelength falling within a narrow wavelength band and transparent to energy at other wavelengths. Consequently, the mirrors and lenses are transparent to visible light. An aiming laser 20 (for example, a conventional helium-neon laser) which generates visible light may be placed in series with IR laser 21 to generate a visible light beam. This light beam may be used to align mirrors 10 and 12 and to adjust focussing lens 22 so that the optical fiber system can be aligned prior to performing surgery.

Also, the optical fibers used to transmit the IR energy from laser 21 to the surgical area can also be used to transmit the visible light from the aiming laser 20 to the surgical area. Thus, when the inventive system is used in performing surgery where the surgical area is visible to the surgeon, the light produced by laser 20 passes through the optical fiber in catheter 30 and can be used to aim the probe tip before laser 21 is turned on to perform the actual operation.

The second lumen in catheter 30 is provided for transmission of a flushing fluid or to apply suction to the probe lens tip area to clear the area of blood during surgery. This latter lumen is connected through bifurcation fitting 28 to a second tube 29. Tube 29 may illustratively be terminated by a standard Luer-Lok fitting 26 which allows connection of the catheter to injectors and standard flow fittings. Solutions injected into the catheter through tube 29 pass through the lumen in catheter 30 and exit at the distal end via a small orifice 32.

Probe tip 34 consists of a lens arrangement which forms the laser energy into a beam 36 which is used to perform the surgical operations. An enlarged view of the probe tip is shown in FIGS. 6 and 7.

To ensure that the distal end of optical fiber 18 is spaced and oriented in a precise position with respect to the end of the probe, fiber 18 is mounted in a high-precision holder 58 which has a reduced diameter end 64 that forms a shoulder 68. Shoulder 68, as will hereinafter be described, is used to hold the probe tip assembly together. Holder 58 has a precision-formed axial bore made up of two sections, including a large-diameter section 60 and a narrow-diameter section 63. Holder 58 may be made of glass, ceramic or other material capable of being formed to specified dimensions with precise tolerances.

Figure 7:
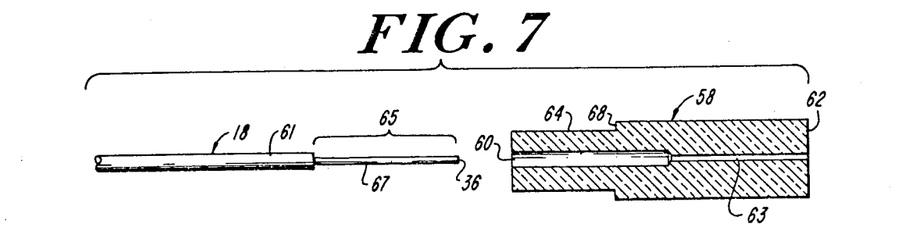
FIG. 7 is an exploded view of a portion of the enlarged cross-section of the probe tip shown in FIG. 6.

In order to attach holder 58 to the end of fiber 18, the fiber is first prepared as shown in FIG. 7. More particularly, prior to insertion of fiber 18 into holder 58, a portion of buffer sheath 61 is removed, exposing a length of optically-conductive core 65. Care is taken when stripping buffer sheath 61 from the fiber not to damage the layer of reflective cladding 67 located on the surface of core 65. After stripping, fiber 18 is inserted into holder 58 so that core 65 extends into the small-diameter bore 63 and sheath 61 extends into the large-diameter bore 60. After fiber 18 has been inserted into holder 58, it may be fastened by epoxy cement to permanently affix the components. To complete the assembly, the end of fiber 18 which protrudes beyond surface 62 of holder 58 may be finished flush with the surface by grinding the assembly or by carefully cleaving the fiber.

Figure 6:
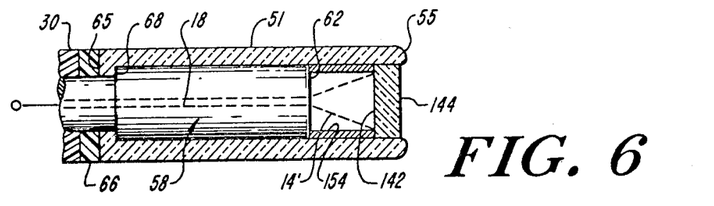
FIG. 6 of the drawing is an enlarged cross-section of the probe tip the single fiber catheter shown in FIG. 5.

Referring to FIG. 6, holder 58 (with fiber 18 fastened inside) is mounted within a glass tube 51 to shield the assembly. The front surface, 62, of holder 58 is spaced from the inner surface 142 of planar lens 144, which may be comprised of glass or sapphire, by means of a spacing ring 154. Ring 154 may illustratively be made of radiopaque material so that the catheter tip can be located inside the patient by means of a fluoroscope.

Glass tubing 51 is bent over shoulder 68 of holder 58 to form a constricted end, 65, which holds the probe tip assembly together. A filler, 66, which may be made of a plastic such as TEFLON (trademark of the DuPont corporation for polytetrafluoroethylene) fills the annular space between catheter body 30 and end 65 of glass tube 51. The outer diameter of the entire assembly from catheter body 30 to glass tube 51 is substantially the same, providing a smooth, uniform surface along the entire length of the catheter as indicated in FIG. 6.

Figure 8:
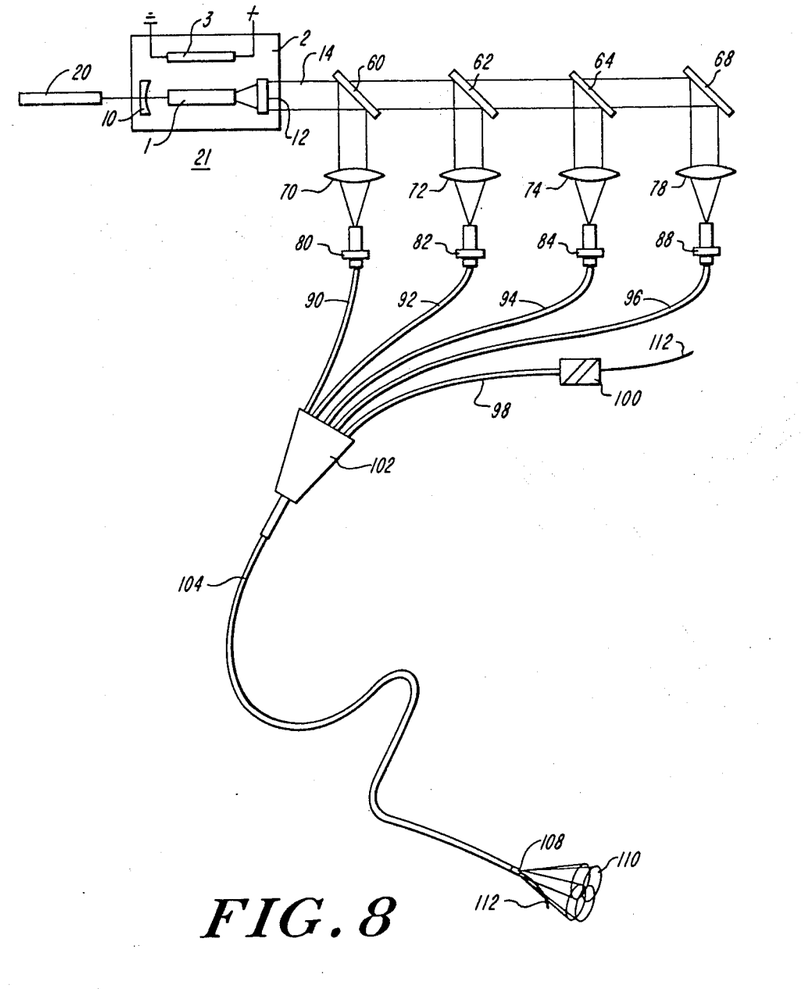
FIG. 8 is a schematic diagram of a wire-guided catheter which employs four optical fibers to increase the area which can be irradiated with the laser light.

FIG. 8 shows a schematic diagram of a wire-guided, four-fiber catheter for use with the present invention. The laser system is set up as previously described with the infrared laser 21 constructed in accordance with the above disclosure. A visible helium-neon aiming laser 20 may also be used in line with laser 21 for aiming purposes as discussed with the single fiber catheter. The output of the infrared laser 21 is directed towards a set of four mirrors 60-68 arranged at a 45° angle with respect to the axis of beam 14.

The first mirror, 60, has a 25% reflective surface and directs approximately ¼ of the energy to focusing lens 70. The second mirror of the set, 62, is a 33% reflector which directs ¼ of the total energy to focusing lens 72. Mirror 64 is a 50% reflector which directs ¼ of the total laser output to focusing lens 74. The last mirror in the set, mirror 68, is a 100% reflector which directs the remaining ¼ of the total energy to focusing lens 78. Mirrors 60-68 and lenses 70-78 are conventional devices.

Focusing lenses 70-78 focus the output energy from IR laser 21 onto four fiber optic connectors 80-88. Connectors 80-88 are connected, respectively, to tubes 90-96 which are all connected, via a branch connector 102, to catheter 104. Each of tubes 90-96 contains a single optical fiber which transmits ¼ of the total laser output energy through the catheter body to the catheter tip 108. An additional tube 98 is provided which is connected to branch fitting 102 and to a conventional Luer Lok connector, 100. This latter tube is connected to a central lumen in catheter body 104 through which flushing solutions may be injected or through which a guide wire may be inserted through the catheter for purposes of guiding the catheter to the surgical area.

At catheter tip 108, the four optical fibers which pass through the catheter are arranged symmetrically so that the beams 110 overlap to illuminate a larger area. Tip 108 also has a hole on the center thereof, through which guidewire 112 can protrude to direct the catheter to the proper location.

Figure 9:
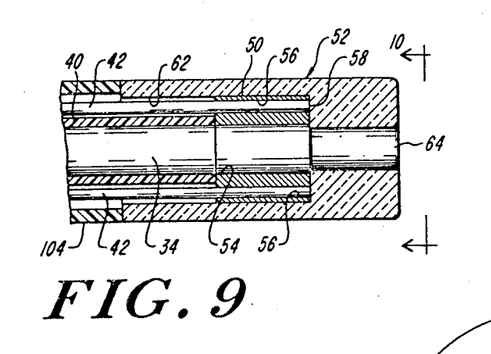
FIG. 9 of the drawing is an enlarged cross-sectional view of the probe tip of the catheter shown in FIG. 7 showing the four optical fibers.
Figure 10:
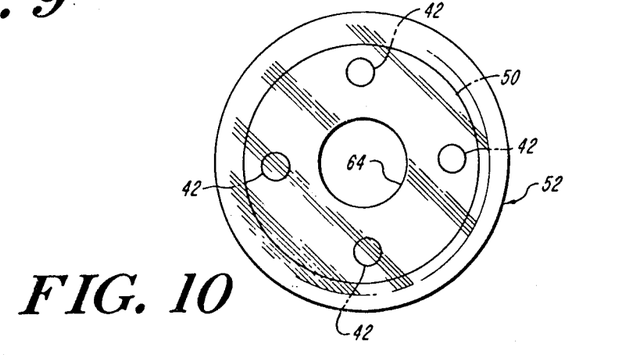
FIG. 10 is an end view of the probe tip of the catheter in the direction 10—10 of FIG. 9.

FIGS. 9 and 10 show detailed views of the illustrative four-fiber catheter tip. The four optical fibers 42 and the inner shaft 40 which holds the fibers, are held in a fiber holder 50 which is preferably formed from a radiopaque material such as stainless steel or platinum. Fiber holder 50 is cylindrical and is provided with a central aperture, 54, which communicates with a lumen 34 of approximately the same size that passes through the center of the catheter body 104. Fiber holder 50 is provided with a plurality of longitudinally extending holes 56 which extend through the wall of holder 50 and receive, in a snug fit, the distal ends of the fiber cores 42. The distal face 58 of the combined fiber cores 42 and holder 50 is polished flat to butt flush against optically transparent cap 52.

Cap 52 is cylindrical and has the same outer diameter as catheter body 104 so that the two pieces define a smooth and continuous diameter. Cap 52 may be formed of a transparent substance such as pyrex glass or sapphire and has an enlarged bore 62 extending in from its proximal end. Bore 62 terminates at its end to form internal shoulder 60. A smaller diameter central aperture, 64, is formed in the distal end of cap 52 which aperture may have the same diameter as aperture 54 in fiber holder 50 and lumen 34 in catheter body 104 to provide a smooth and continuous lumen which opens at the distal tip of the catheter. However, the aperture 64 in tip 52 may also be somewhat narrower than aperture 54 and lumen 34 as long as sufficient clearance is provided to accommodate a guidewire without adversely interfering with fluid flow and pressure measurements.

Cap 52 is secured by an epoxy adhesive (placed on its inner surface 62) to the fiber holder 50 and also to the portion of the inner shaft 40 and fibers 42 which are disposed within the proximal end of the cap 52. The distal end of the catheter body 104 is heat shrunk around the inner shaft 40 and fibers 42 to provide a smooth transition from cap 52 to catheter body 104.

More complete construction details of a four fiber catheter suitable for use with the illustrative embodiment are given in co-pending U.S. patent application entitled "Wire Guided Laser Catheter", filed on May 22, 1985 by Stephen J. Herman, Laurence A. Roth, Edward L. Sinofsky and Douglas W. Dickinson, Jr.

Figure 11:
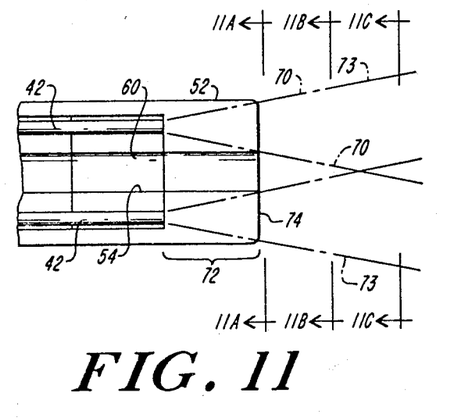
FIGS. 11, 11A, 11B, and 11C are schematic diagrams of the beam pattern produced by the four-fiber catheter at the surgical location.

FIG. 11 illustrates the output beam pattern developed by a four-fiber catheter, such as that described above, in which the four fibers are arranged in two diametrically-opposed pairs. The beam pattern from each of the four fiber ends is defined by a cone formed by the ray lines 70 in FIG. 11. The beam from each individual fiber 42 is emitted from the distal face of the fiber 42 and enters the distal segment 72 of cap 52 through the face defining the shoulder 60. The beam from each fiber is divergent and, in the illustrative embodiment, may have a half-angle in the range of 6°-16°, depending on the numerical aperture of the fibers which are used to construct the catheter.

Figure 11A:
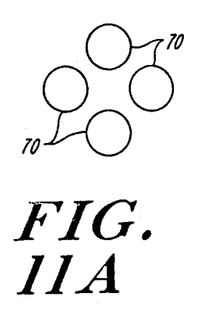
Figure 11B:
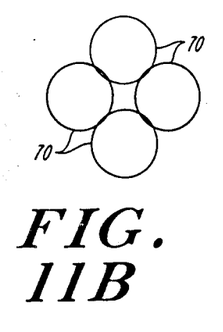
Figure 11C:
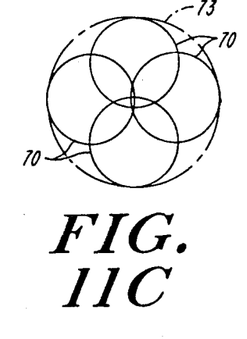

The diverging beam from each of the fibers 42 exits from the distal emission face 74 at the end of cap 52. FIGS. 11A, 11B and 11C illustrate the overall beam pattern (in cross-section) which is formed by the output of the four fibers as seen along image planes 11A, 11B and 11C in FIG. 11. At plane 11A, which is located at the emission face 74 of cap 52, the four beams in the illustrative embodiment are still separate. At plane 11B, the diverging beams have spread further and have begun to overlap. At the plane indicated as 11C, the beams have overlapped and define an envelop 73 having an outer diameter which is slightly greater than the outer diameter of the catheter body 104. Preferably, at plane 11C, beams 70 will have overlapped to merge and cover a continuous pattern. Illustratively, such a merger will have occurred within a distance from the distal face 74 of tip 52 which is approximately equal to the outer diameter of catheter 104 (a typical diameter is 1.5 millimeters).

A preferred application of the previously described laser catheter system of this invention is the removal of atherosclerotic plaque. The laser must be operated in a pulsed mode to remove such plaque. A continuous wave laser is unsuitable for plaque removal, since a continuous wave laser transmits insufficient energy to the surgical site at a time to vaporize the tissue before the energy is dissipated by thermal diffusion. As a consequence, typically, carbon deposits are formed in the affected area, and it is difficult to cleanly and accurately remove plaque from artery walls using a continuous wave laser.

Although any of the lasers previously mentioned as operating in the preferred range of wavelengths would be suitable for the removal of atherosclerotic plaque, it has been found that Holmium doped lasers operating at a wavelength in the range of from about 1.90 to 2.10 micrometers are particularly suited for such surgical applications. In the first place, Holmium-doped lasers operate in the preferred range of wavelengths of 1.4–2.2 micrometers, and they can be operated in a pulsed mode. Secondly, Holmium-doped lasers are generally very efficient, generating 10 watts of average power for every kilowatt of electrical power supplied to the lamp. Because of these power requirements, which are lower than for most conventional lasers, no open loop cooling is required. Furthermore, such lasers can be operated with a conventional 110 volt power source. As a consequence of the foregoing, Holmium-doped laser sources often are portable, and can be operated either in a hospital environment, or in a doctor's office, or even in the home. A laser source which is preferred is a Holmium-doped Yttrium-Scandium-Gadolinium Garnet (YSGG) laser operating at a wavelength of 2.088 micrometers. Such a laser can remove any tissue containing water.

The pulse width of any laser which is used for plaque removal should be substantially less than the thermal time constant for that particular tissue. Typically, the pulse width should be roughly an order of magnitude less than the thermal time constant. For wavelengths in the range of 1.4–2.2 micrometers, thermal diffusion, which is a function of absorption, is reduced to an insignificant factor when such pulse widths are used. For a given power or energy level delivered per pulse, pulses longer than the thermal time constant will be generally incapable of precisely removing tissue, because the energy delivered thereby will be dissipated through thermal diffusion.

For all tissue, the thermal time constant is equal to the absorption length of that particular tissue type squared over four times its thermal diffusivity. For most tissue, the thermal diffusivity is equal to about $1 \times 10^{-3}$ cm$^2$/sec, while for atherosclerotic plaque, the thermal diffusivity is equal to about $1.2 \times 10^{-3}$ cm$^2$/sec. The absorption length for most types of plaque is about $2 \times 10^{-2}$ cm. Thus, for plaque, the thermal time constant is approximately $8.3 \times 10^{-2}$ seconds. Therefore, typically, the pulse width should be of the order of about 8.3 milliseconds or less.

The repetition rate is not critical, and typically is in the range of 1–10 Hertz. The preferred rate, for use with a Holmium-doped laser, is about 2 Hertz.

The energy density delivered is defined as the energy per pulse divided by the spot size. The spot size is the area of the spot upon which the laser energy is incident. It has been predicted theoretically and verified experimentally that for plaque removal, the energy density of each pulse should exceed some threshold value. If the energy density is less than this threshold value, the energy will be dissipated by thermal diffusion before the tissue is vaporized, and no vaporization will occur. It has been found that most energy densities above the threshold value can be used, up to the operational limit of the laser and the associated fiber optic system.

The threshold value of the energy density for plaque will vary, depending upon the particular tissue sample invoved. Generally, tissue samples with more calcification or less water content will vaporize at a higher threshold value, while tissue samples with less calcification, or a higher water content, will vaporize at a lower threshold value.

A thermal model was developed for laser pulses whose pulse widths are small compared to the thermal time constant of the material with which the laser is to be used. Using this thermal model, one can develop predicted threshold energy densities per pulse for lasers operating at different wavelengths, as well as the extent of thermal damage or the extent of the denatured rim.

In using this thermal model, the energy profile in the tissue can be described as a function with separable axial and radial components. The axial component can be described by the attenuation coefficient according to Beer's law and the radial component can be described by a linearly expanding Gaussian distribution. The axial and radial components can be defined mathematically as follows:

$$J(r,z) = J(r) \cdot J(z)$$

where
$$J(z) = J_o e^{-\alpha z}$$

and
$$J(r)=e^{-2r^2/x^2},$$

where the function J(r,z) is the spatial energy distribution, z is the axial distance into the tissue measured from the tissue-air or tissue-water interface, α is the combined absorption-scattering attenuation coefficient, r is the radial distance measured from the optical axis, and x is the $1/e^2$ beam width of the Gaussian-like radial light distribution.

The amount of energy, ΔJ, deposited into a volume element is equal to the energy profile divided by the volume as a function of the radial distance measured from the optical axis or $$\frac{\Delta J}{V} = \frac{J(\Delta r) \, J(\Delta z)}{V(\Delta r)}$$

Besides the attenuation coefficient, the next most important parameter is a description of the $1/e^2$ radius, x. Beam spreading occurs due to multiple scattering. Measurements have shown that the beam spreading is linear in almost all cases, although the slope varies with different tissue samples. Because absorption dominates over scattering in mid-infrared wavelengths, spreading in this range should be quite small. Therefore, it is assumed that the radius expands with the same divergence as the incident beam.

The threshold energy density is the sum of the energy required to raise the tissue temperature to 150° C. from the ambient temperature of about 37° C. plus the energy required to overcome the heat of vaporization (2260 J/g). Thus, $$\frac{\Delta J}{V} = \rho c \Delta T + L_v \rho$$

where p is the tissue density (1.2 g/cm³), c is the specific heat (3.6 J/g°C.), and $L_v$ is the heat of vaporization (2260 J/g). It can be seen that the total energy density required to vaporize a volume element is 3200 J/cm³. When the deposited energy density is between 488 and 3200 J/cm³, the tissue temperature remains at 150° C.

For purposes of comparison, the vaporization threshold is defined as being reached if enough energy is supplied to vaporize tissue out to the edge of a 1 millimeter hole. This definition means that both the central peak and the wings of the Gaussian energy distribution are sufficient to vaporize tissue. The thermal zone of damage is defined as the region in which the temperature has reached above 60° C., and can vary in the axial and radial directions. Energy densities in terms of joules/mm² for different wavelengths can be determined based on the assumption that the depth of the hole is equal to the absorption length of the radiation at that wavelength.

Based upon the foregoing analysis, the following Table I sets forth the predicted threshold energy densities in joules per mm² and the predicted sizes of the zones of axial and radial thermal damage in micrometers for the lasers previously indicated to operate within the preferred rang of wavelengths. All of these predicted energy densities are for atherosclerotic plaque having a high water content and little or no calcification.

TABLE I

| Laser | Wave-Length (μm) | Absorption Coeff (cm⁻¹) | Threshold Energy Density (J/mm²) | Thermal Damage (μm) Axial | Thermal Damage (μm) Radial |
|---|---|---|---|---|---|
| Ho:YAG | 2.1 | 50 | .76 | 500 | 500 |
| Ho:YSGG | 2.088 | 50 | .76 | 500 | 500 |
| Er:YAG | 1.55 | 2700 | .0095 | 12 | 12 |
| Ho:YLF | 2.06 | 50 | .76 | 100 | 300 |
| Tm:YAG | 1.88 | 50 | .76 | 100 | 300 |
| Er:YLF | 1.73 | 15 | 5.7 | 500 | 300 |

Energy densities required to vaporize atherosclerotic plaque using a Holmium-doped laser also have been determined empirically from the experimental data. These threshold energy densities were determined using an apparatus 120 shown schematically in FIG. 12. Apparatus 120 includes a laser source 122, focusing lens and fiber optic connector 124, fiber optic 126, and a tank 128 containing the tissue sample 130. Laser source 122 and connector and associated lens 124 are both conventional, as previously described with respect to FIGS. 3-11. Fiber optic 126 may contain a single optical fiber, or it may contain a bundle of optical fibers. Typically, in conducting these experiments, a single fiber was used.

Figure 12:
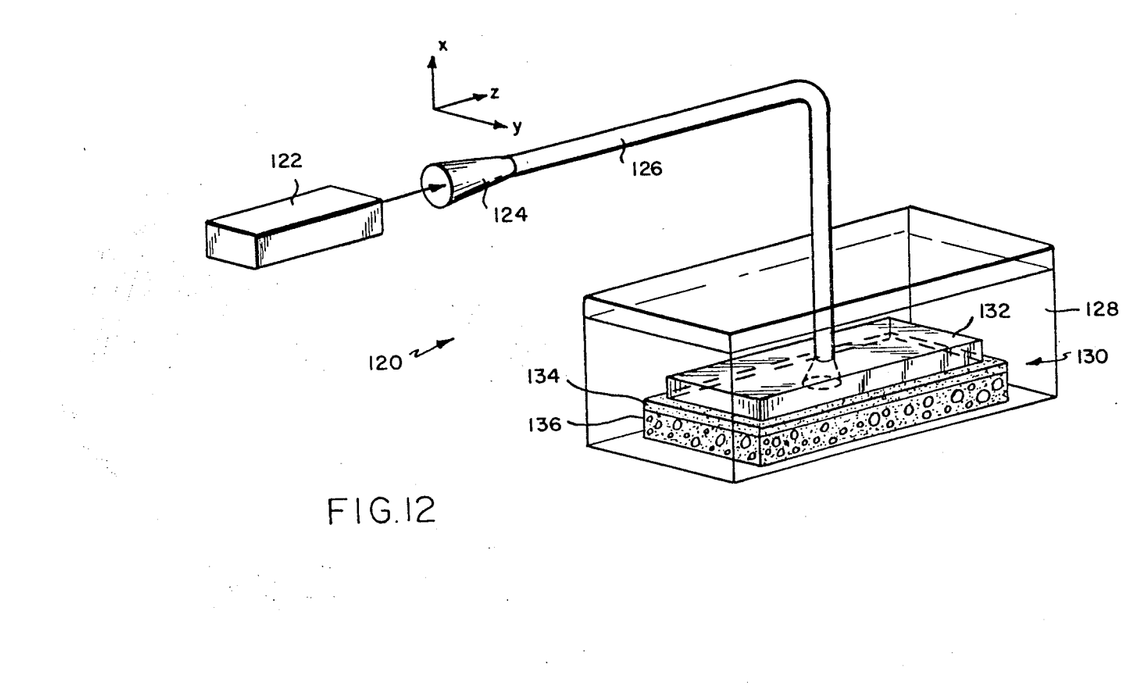
FIG. 12 is a schematic diagram illustrating the apparatus used to obtain in vitro data relating to the removal of atherosclerotic plaque.

Tank 128 contains a saline solution in which the tissue sample 130 is immersed. Each optical fiber included within fiber optic 126 typically is a 100 micron fiber. Also immersed in the saline solution in tank 128 and covering tissue sample 130 is a sapphire plate 132. The end of fiber optic 126 is placed in direct contact with the upper surface of plate 132, while the lower surface of plate 132 is in direct contact with the tissue sample. In conducting these experiments, typically the sapphire plate 132 had a thickness of 1.52 millimeters. The sapphire plate 132 is used to permit a controlled spreading of the beam of light emitted from the end of fiber optic 126 to produce the desired spot size on the tissue sample.

Tissue sample 130 used in each of these experiments comprises a layer of a fatty fibrous plaque 134 disposed on top of a section of an aorta wall 136. Two different tissue samples were used. Experiments 1-9 were performed on Sample No. 2 while experiments 10-13 were performed as Sample No. 1. Sample No. 1 exhibited greater calcification and lower water content than Sample No. 2. Sample No. 2 exhibited virtually no calcification and a high water content. Prior to use, the tissue samples had been removed from the body, and had been carefully frozen and stored at a temperature of −70° C. The tissue samples were later thawed for use in these experiments over a lengthy period of time to avoid damage to the tissue and to avoid destruction of the cells during the freezing and thawing processes.

In each experiment, a Holmium doped YSGG laser was operated in a pulsed mode at a wavelength of 2.088 micrometers. The pulse width used was 400 microseconds, and two pulses were emitted for each test with a spacing of one half second, or at a rate of 2 Hertz. The spot sizes and energies per pulse were varied to determine the threshold energy density. The results of these experiments are set forth below in Table II.

TABLE II

| Experiment | Energy/Pulse, (Joules) | Delivery Area, (mm$^2$) | Fluence, Ablation (Joules/Area, mm$^2$) | (mm$^2$) | OD, (mm) | Thermal, Damage (mm) |
|---|---|---|---|---|---|---|
| 1 | $122 \times 10^{-3}$ | $4.012 \times 10^{-1}$ | 0.304 | N/A | N/A | N/A |
| 2 | $222.5 \times 10^{-3}$ | $4.012 \times 10^{-1}$ | 0.555 | N/A | N/A | N/A |
| 3 | $310 \times 10^{-3}$ | $4.012 \times 10^{-1}$ | 0.773 | $3.848 \times 10^{-1}$ | $100 \times 10^{-6}$ | $50 \times 10^{-6}$ |
| 4 | $816.2 \times 10^{-3}$ | $3.14 \times 10^{-2}$ | 25.98 | $6.158 \times 10^{-2}$ | $280 \times 10^{-6}$ | $240 \times 10^{-6}$ |
| 5 | $475 \times 10^{-3}$ | $3.14 \times 10^{-2}$ | 15.13 | $4.337 \times 10^{-2}$ | $235 \times 10^{-6}$ | $240 \times 10^{-6}$ |
| 6 | $268.7 \times 10^{-3}$ | $3.14 \times 10^{-2}$ | 8.55 | $5.41 \times 10^{-3}$ | $262.5 \times 10^{-6}$ | $100 \times 10^{-6}$ |
| 7 | $875 \times 10^{-3}$ | $5.3 \times 10^{-1}$ | 1.65 | $5.03 \times 10^{-1}$ | $800 \times 10^{-6}$ | $35 \times 10^{-6}$ |
| 8 | $760 \times 10^{-3}$ | $5.3 \times 10^{-1}$ | 1.434 | $6.36 \times 10^{-1}$ | $900 \times 10^{-6}$ | $35 \times 10^{-6}$ |
| 9 | $655 \times 10^{-3}$ | $3.14 \times 10^{-2}$ | 20.85 | $1.018 \times 10^{-1}$ | $360 \times 10^{-6}$ | $200 \times 10^{-6}$ |
| 10 | $185 \times 10^{-3}$ | $3.14 \times 10^{-2}$ | 5.89 | $6.157 \times 10^{-2}$ | $280 \times 10^{-6}$ | $35 \times 10^{-6}$ |
| 11 | $139 \times 10^{-3}$ | $3.14 \times 10^{-2}$ | 4.43 | $4.869 \times 10^{-2}$ | $249 \times 10^{-6}$ | $10 \times 10^{-6}$ |
| 12 | $271 \times 10^{-3}$ | $3.14 \times 10^{-2}$ | 8.63 | $4.869 \times 10^{-2}$ | $249 \times 10^{-6}$ | $25 \times 10^{-6}$ |
| 13 | $74.5 \times 10^{-3}$ | $3.14 \times 10^{-2}$ | 2.37 | N/A | N/A | N/A |

The value for the energy per pulse in Table II was measured in a conventional manner. The delivery area in square millimeters was calculated from the known, controlled spreading of the light beam as it passed from fiber optic 126 through sapphire plate 132. The fluence, in joules per square millimeter was calculated by dividing the energy per pulse by the delivery area. The ablation area is the area of the hole formed in the tissue sample. The extent of thermal damage is the distance beyond the rim of the hole where thermal damage was observed, while the OD is the outside diameter of the hole formed. The ablation area, OD and extent of thermal damage were all measured microscopically from histological slides prepared from the specimens using conventional histological techniques.

The immersion of a tissue sample in a saline solution, as shown in FIG. 12, closely models the conditions inside the body. Although all of these experiments were conducted in vitro, as shown, one could expect nearly identical results in vivo.

It can be seen from Table II that, for fatty fibrous plaque, having a high water content and virtually no calcification, the threshold energy density per pulse is at least about 0.6 J/mm$^2$ for a Holmium-doped YSGG laser operating at a wavelength of 2.088 micrometers. It is expected that similar experiments using a Ho:YAG laser and a Ho:YLF laser would show that the energy threshold for such lasers is also at least about 0.6 J/mm$^2$ per pulse at their respective wavelengths of operation, based upon the fact that identical threshold energy densities are predicted by the theoretical model, as shown in Table I.

For the other lasers described herein as being suitable, the theoretically predicted threshold energy densities per pulse for vaporization of fatty fibrous plaque having virtually no calcification and a high water content are as follows as found in Table I: Erbium YAG, 9.5 mJ/mm$^2$; Erbium YLF, 5.7 J/mm$^2$; and Thulmium YAG, 0.76 J/mm$^2$. The precise threshold energy density depends upon the wavelength, and the degree of calcification and water content of the tissue sample. As indicated, the greater the calcification and the less the water content, the higher the threshold energy density required for vaporization of the tissue.

The data set forth in Tables I and II also illustrate additional advantages of using a Holmium-doped laser within the wavelength ranges of 1.90 micrometers to 2.1 micrometers. It can be seen that the zone of thermal damage is minimal, far less than one would expect from the prior art. Furthermore, virtually no carbonization was observed in each of the experiments. Such superior results were not achieved in tests with any other existing laser source which could be delivered via a non-toxic, durable, flexible fiber optic to a vein or artery within the body.

In view of the above description, it is likely that modifications and improvements may occur to those skilled in the art within the scope of this invention. Thus, the above description is intended to be exemplary only, the scope of the invention being described by the following claims and their equivalents.

What is claimed is:

1. A system for the surgical removal of atherosclerotic plaque comprising:
   a laser energy source operating in a pulsed mode with an output wavelength in the range of from about 1.4 to about 2.2 micrometers, said laser energy source operating at an energy density of at least about 0.6 joules per square millimeter per pulse;
   an optical fiber;
   means for coupling an output of said laser source to a proximal end of said optical fiber; and
   means attached to a distal end of said optical fiber for directing laser energy propagating down said optical fiber to a surgical site within the body.

2. A system as recited in claim 1 wherein said laser energy source comprises a Holmium-doped laser with an output wavelength in the range of from about 1.9 to about 2.1 micrometers.

3. A system as recited in claim 1 wherein said laser energy source is a Holmium doped Yttrium-Scandium-Gadolinium Garnet laser having an output wavelength of 2.088 micrometers.

4. A system as recited in claim 1 wherein the pulse width of each pulse is substantially less than about 83 milliseconds.

5. A system as recited in claim 4 wherein the pulse width is of the order of about 8 milliseconds.

6. A system as recited in claim 1 wherein said optical fiber comprises a silica fiber purified to reduce the hydroxyl ion content as low as possible.

7. A system as recited in claim 1 wherein said laser source comprises a Holmium-doped Yttrium-Aluminium-Garnet laser.

8. A system as recited in claim 1 wherein said laser source comprises a Holmium doped Yttrium-Lithium-Fluoride laser.

9. A system as recited in claim 1 wherein said laser source comprises an Erbium-doped Yttrium-Lithium-Fluoride laser.

10. A system as recited in claim 1 wherein said laser source comprises a Thulium doped Yttrium-Aluminium-Garnet laser.

11. A system as recited in claim 1 further comprising an aiming laser source generating a visible light output and means for directing said visible light output through said laser source and said optical fiber to align said laser and said fiber to visually illuminate said surgical site.

12. A system as recited in claim 1 wherein said optical fiber further comprises:
- a plurality of optical fibers having proximal and distal ends;
- a plurality of partially reflective mirrors arranged in series along an axis of an output beam emitted by said laser source for directing a portion of said output beam of said laser source to said proximal ends of said optica fibers; and
- a plurality of focusing lenses positioned between said mirrors and said proximal ends of said fibers for focusing portions of said laser output to said proximal ends of said fibers;
- said directing means holding said fibers in a fixed position relative to one another so that optical beams emanating from said distal ends of said fibers overlap to cover an area at least equal to the diameter of said directing means.

13. A system for the surgical removal of atherosclerotic plaque comprising:
- a Holmium-doped laser energy source operating in a pulsed mode with an output wavelength in the range of from about 1.90 to about 2.1 micrometers, said laser energy source operating at an energy density of at least about 0.6 joules per square millimeter per pulse, said laser being operated with a pulse width substantially less than about 83 milliseconds and at a repetition rate in the range of from about 1 to about 10 Hertz;
- an optical fiber;
- means for directing an output of said laser source to a proximal end of said optical fiber; and
- means attached to a distal end of said optical fiber for directing laser energy propagating down said optical fiber to a surgical site.

14. A system of the surgical removal of atherosclerotic plaque comprising:
- an Erbium-doped YAG laser energy source operating in a pulsed mode with an output wavelength of about 1.55 micrometers, said laser energy source operating at an energy density of at least about $9.5 \times 10^{-3}$ joules per square millimeter per pulse, said laser energy source being operated with a pulse width substantially less than about 83 milliseconds and at a repetition rate in the range of from about 1 to about 10 Hertz;
- an optical fiber;
- means for directing an output of said laser source to a proximal end of said optical fiber; and
- means attached to a distal end of said optical fiber for directing laser energy propagating down said optical fiber to a surgical site.

15. A system for the surgical removal of atherosclerotic plaque comprising:
- an Erbium-doped YLF laser energy source operating in a pulsed mode with an output wavelength of about 1.73 micrometers, said laser energy source operating at an energy density of at least about 5.7 joules per square millimeter per pulse, said laser energy source being operated with a pulse width substantially less than about 83 milliseconds and at a repetition rate in the range of from about 1 to about 10 Hertz;
- an optical fiber;
- means for directing an output of said laser source to a proximal end of said optical fiber; and
- means attached to a distal end of said optical fiber for directing laser energy propagating down said optical fiber to a surgical site.

16. A system for the surgical removal of atherosclerotic plaque comprising:
- a Thulium-doped YAG laser energy source operating in a pulsed mode with an output wavelength of about 1.88 micrometers, said laser energy source operating at an energy density of at least about 0.76 joules per square millimeter per pulse, said laser energy source being operated with a pulse width substantially less than about 83 milliseconds and at a repetition rate in the range from of about 1 to about 10 Hertz;
- an optical fiber;
- means for directing the output of said laser source to a proximal end of said optical fiber; and
- means attached to a distal end of said optical fiber for directing laser energy propagating down said optical fiber to a surgical site.

* * * * *